United States Patent
Heeney et al.

(10) Patent No.: US 6,824,706 B2
(45) Date of Patent: Nov. 30, 2004

(54) MONO-, OLIGO- AND POLY-DIFLUOROVINYL-(HETERO)ARYLENES, THEIR SYNTHESIS AND THEIR USE AS CHARGE TRANSPORT MATERIALS

(75) Inventors: Martin Heeney, Southampton (GB); Louise Farrand, Blandford Forum (GB); Mark Giles, Southampton (GB); Marcus Thompson, Hampshire (GB); Steven Tierney, Southampton (GB); Maxim Shkunov, Southampton (GB); David Sparrowe, Dorset (GB); Iain McCulloch, Hampshire (GB)

(73) Assignee: Merck Patent Gesellschaft mit beschrank Haftung, Darmstadt (DE)

( * ) Notice: Subject to any disclaimer, the term of this patent is extended or adjusted under 35 U.S.C. 154(b) by 55 days.

(21) Appl. No.: 10/201,574

(22) Filed: Jul. 24, 2002

(65) Prior Publication Data

US 2003/0062536 A1 Apr. 3, 2003

(30) Foreign Application Priority Data

Jul. 25, 2001 (EP) ............................................ 01117650

(51) Int. Cl.$^7$ ............................................. C09K 19/52
(52) U.S. Cl. .................... 252/299.01; 349/183; 568/74; 568/77; 568/775
(58) Field of Search ........................ 252/299.01–299.7; 349/183; 568/74–77, 775

(56) References Cited

U.S. PATENT DOCUMENTS 5,198,153 A     3/1993   Angelopoulos et al.
5,380,461 A  *  1/1995   Sato et al. ............. 252/299.61
5,723,682 A  *  3/1998   Poetsch et al. ............. 568/655
5,892,244 A     4/1999   Tanaka et al.
5,998,804 A    12/1999   Suh et al.
6,174,457 B1 *  1/2001   Kato et al. ............. 252/299.63

FOREIGN PATENT DOCUMENTS

| DE | 195 04 224 | 8/1995 |
| EP | 0 261 712 | 3/1988 |
| EP | 0 528 662 | 2/1993 |
| EP | 0 889 350 | 1/1999 |
| GB | 2 303 633 | 2/1997 |
| WO | WO 93/22397 | 11/1993 |
| WO | WO 95/22586 | 8/1995 |
| WO | WO 96/21659 | 7/1996 |
| WO | WO 97/00600 | 1/1997 |
| WO | WO 00/79617 | 12/2000 |

* cited by examiner

*Primary Examiner*—Mark F. Huff
*Assistant Examiner*—Jennifer R Sadula
(74) *Attorney, Agent, or Firm*—Millen White Zelano & Branigan, P.C.

(57) ABSTRACT

The invention relates to new mono-, oligo- and poly-difluorovinyl(hetero)arylenes comprising one or more identical or different recurring units of formula I

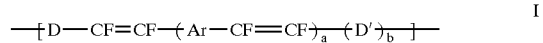

wherein D, D', Ar, a and b have the meanings as defined in herein. Furthermore the inventions relates to their synthesis, their use as semiconductors or charge transport materials and their different applications.

34 Claims, No Drawings

MONO-, OLIGO- AND POLY-DIFLUOROVINYL-(HETERO)ARYLENES, THEIR SYNTHESIS AND THEIR USE AS CHARGE TRANSPORT MATERIALS

FIELD OF INVENTION

The invention relates to new mono-, oligo- and poly-difluorovinyl-(hetero)arylenes, polymerisable liquid crystal materials and anisotropic polymer films, including their oxidatively or reductively doped forms. The invention further relates to methods of their preparation, their use as semiconductors or charge transport materials in optical, electrooptical or electronic devices including field effect transistors, electroluminescent, photovoltaic and sensor devices. The invention further relates to field effect transistors and semiconducting components comprising the new mono-, oligo- and poly-difluorovinyl-(hetero)arylenes. Furthermore the invention relates to a security marking or device and to a charge injection layer, planarising layer, antistatic film or conducting substrate or pattern. The invention also relates to their synthesis and to a key intermediate compound.

BACKGROUND AND PRIOR ART

Organic materials have recently shown promise as the active layer in organic based thin film transistors and organic field effect transistors (OFETs) [see reference 1]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semiconducting material and the current on/off ratio, so the ideal semiconductor should have a low conductivity in the off state, combined with a high charge carrier mobility ($>1\times10^{-3}$ cm$^2$ V$^{-1}$ s$^{-1}$). In addition, it is important that the semiconducting material is relatively stable to oxidation, i.e., it has a high ionisation potential, as oxidation leads to reduced device performance. A known compound which has been shown to be an effective p-type semiconductor for OFETs is pentacene [see reference 2]. When deposited as a thin film by vacuum deposition, it was shown to have carrier mobilities in excess of 1 cm$^2$ V$^{-1}$ s$^{-1}$ with very high current on/off ratios greater than $10^6$. However, vacuum deposition is an expensive processing technique that is unsuitable for the fabrication of large-area films.

In general, poly(3-alkylthiophenes) show improved solubility and are able to be solution processed to fabricate large area films. The 3-alkyl substituents can be incorporated in a polymer chain with two different orientations: head-to-tail linkage (HT) or head-to-head (HH). A high regioregularity leads to improved packing and optimised microstructure, leading to improved charge carrier mobility [see reference 3, 4, 5]. However, poly(3-alkylthiophenes) have relatively low ionisation potentials and are susceptible to doping in air [see reference 6].

Regioregular poly(3-hexylthiophene) has been reported with charge carrier mobility between $1\times10^{-5}$ and $4.5\times10^{-2}$ cm$^2$ V$^{-1}$ s$^{-1}$, but with a rather low current on/off ratio ($10$–$10^3$) [see reference 7].

Fluorinated poly(alkylthiophenes) were studied by L. Robitaille and M. Leclerc [see reference 8]. Poly[3-(tridecafluorononyl)thiophene] was found to be soluble in octafluorotoluene. Compared to its alkyl analogues, however, it exhibited inferior electronic properties, which was attributed to lower regioregularity.

Poly(p-phenylene vinylene)s (PPV) were studied by S. Doi et al. [see reference 9] and observed to be efficient as light emitting and hole transport materials. Furthermore poly(thienyl vinylene) (PTV) was described as a conducting polymer between an ITO layer and the hole transport material.

Poly(2,5-thienylene vinylene) (PTV) was characterized as a semiconductor in thin-film transistors (TFT) [see reference 10]. The polymer itself is insoluble, infusible and therefore was processed via a soluble precursor, followed by heat treatment. Because of a low ionization potential, p doping with oxygen of the air resulted automatically. But degradation of the polymer, especially thin films, by oxidation reduces the performance of the device [see reference 11]. It was found that the carrier mobility largely depends on the π-conjugation length of PTV and is comparable to that of α-Si TFT.

The manufacture of a field effect transistor (FET) in which a π-conjugated polymer film serves as a semiconductor layer is described in the U.S. Pat. No. 5,892,244 [reference 12]. A polymer precursor film is formed which is soluble in a solvent. Then the precursor film is changed to the π-conjugated polymer film. The polymer is represented by one of the two general formulae:

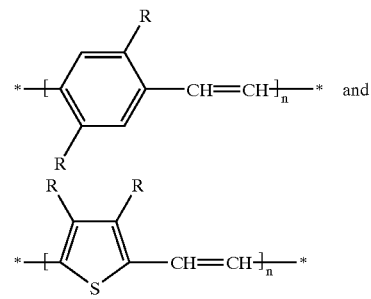

wherein R is H, alkyl or alkoxy.

Compounds and polymers, including their with anions doped forms, having the formula:

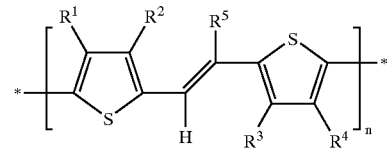

as a recurring unit wherein $R^1$, $R^2$, $R^3$ and $R^4$ are electron donating substituents or hydrogen and $R^5$ is an electron withdrawing substituent, are disclosed in WO 96/21659 [reference 13]. For the synthesis a chemical and a electro-chemical polymerisation is described. Their electrical conductivity and their use in electronic and opto-electronic devices, such as light emitting diodes (LEDs) is mentioned.

Poly(3-dodecylthienylene vinylene)s (PDDTV) were synthesized and the effect of structural regularity was studied by R. D. McCullough and R. S. Loewe [see reference 11]. Preparation by Heck polymerization led to regioirregular PDDTV and by Stille polymerization to at least 90% regioregular, head-to-tail coupled, PDDTV.

The synthesis of poly(2,5-thienylene-F-polyene)s has been described by A. B. Shtrarev and Z. Chvatal [see reference 14]. Reacting 2,5-dilithio- or 2,5-bis(bromomagnesio)thiophenes with F-1,3-butadiene and F-ethylene gave oligomers having the units:

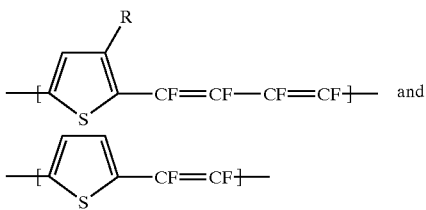

respectively, wherein R is H or CH$_3$.

The 2,5-thienylene-F-ethenylene showed the lowest solubility in ether compared to the corresponding F-butadienylenes. The disubstituted product (E,E)-2,5-bis [2-(2-thienyl)-1,2-difluoroethenyl]-thiophene exhibited a reversible nematic phase.

GB 2303633 relates to a conjugated polymer or oligomer which comprises arylene vinylene units having an aromatic ring or an E-configured vinylidene linking group which bears an electron-withdrawing substituent comprising fluorine or perfluoroalkyl. The preferred trifluoromethyl group, to which the examples refer, is described to stabilize the oligomer and polymer to degradation under illumination and to suppress oxidation, owing to its large steric bulk.

As a result, an improvement of the efficiency of LEDs by incorporating these materials as an emissive or electron-transport layer is claimed.

It is an aim of the present invention to provide new materials for use as semiconductors or charge transport materials, which are easy to synthesize, have high charge mobility, good processibility and improved oxidative stability.

A further aim of the present invention is to provide a synthesis route for the oligo- and polymers according to the invention, resulting in a high regioregularity, and to describe the intermediate compounds. Still another aim of the present invention is novel intermediates and process steps described hereinafter.

Further aims of the present inventions relate to advantageous uses of the mono-, oligo- and polymers, including their oxidatively or reductively doped forms, according to the invention.

Other aims of the invention are immediately evident to those skilled in the art from the following description.

The inventors have found that these aims can be achieved by providing new monomers, oligomers and polymers based on difluorovinyl-(hetero)arylenes.

The incorporation of the two electronegative fluorine substituents on the vinylidene linker increases the electron affinity of the conjugated system. The mono-, oligo- and polymers according to the invention generally show an increased oxidation potential in comparison with the PTV analogues, leading to a lower susceptibility to doping and therefore greater stability. The described materials also exhibit improved solubility and enhanced ordering in comparison to the non alkylated analogues.

Unlike other substituents the small size of the fluorine atom reduces steric strain from the oligomer or polymer backbone, which can cause a deviation from planarity. The mono-, oligo- and polymers according to the invention show a high degree of conjugation and packing, resulting in superior semiconductive properties, especially high charge carrier mobility combined with a large on/off ratio.

A further aspect of the invention relates to reactive mesogens consisting of a central core comprising one or more difluorovinyl-(hetero)arylene units, and optionally comprising further conjugated moieties that form an extended conjugated system together with the difluorovinyl-(hetero)arylene units, said core being linked, optionally via a spacer group, to one or two polymerisable groups. The reactive mesogens can induce or enhance liquid crystal phases or are liquid crystalline themselves. They can be ordered and aligned in their mesophase and the polymerisable group can be polymerised or crosslinked in situ to form coherent polymer films with a high degree of long range order or monodomain, thus yielding improved semiconductor materials with high stability and high charge carrier mobility.

A further aspect of the invention relates to liquid crystal polymers, in particular liquid crystal side chain polymers obtained from the reactive mesogens according to the present invention, which are then further processed e.g. from solution as thin layers for use in semiconductor devices.

A further aspect of the invention relates to the mono-, oligo- and polymers, a material or polymer film according to the invention, which are oxidatively or reductively doped to form conducting ionic species. Another aspect of the invention is a charge injection layer, planarising layer, antistatic film or conducting substrate or pattern for electronic applications or flat panel displays, comprising mono-, oligo- or polymers, a material or polymer film according to this invention.

The synthesis route according to the invention was found to yield oligo- and polymer material with a high to very high regioregularity, especially head-to-tail orientation.

DEFINITION OF TERMS

The terms 'liquid crystalline or mesogenic material' or 'liquid crystalline or mesogenic compound' means materials or compounds comprising one or more rod-shaped, lath-shaped or disk-shaped mesogenic groups, i.e. groups with the ability to induce liquid crystal phase behaviour. The compounds or materials comprising mesogenic groups do not necessarily have to exhibit a liquid crystal phase themselves. It is also possible that they show liquid crystal phase behaviour only in mixtures with other compounds, or when the mesogenic compounds or materials, or the mixtures thereof, are polymerised.

The term 'polymerisable' includes compounds or groups that are capable of participating in a polymerisation reaction, like radicalic or ionic chain polymerisation, polyaddition or polycondensation, and reactive compounds or reactive groups that are capable of being grafted for example by condensation or addition to a polymer backbone in a polymer-analoguous reaction.

The term 'film' includes self-supporting, i.e., free-standing, films that show more or less pronounced mechanical stability and flexibility, as well as coatings or layers on a supporting substrate or between two substrates.

SUMMARY OF THE INVENTION

The invention relates to mono-, oligo- and polymers comprising at least one difluorovinyl-(hetero)arylene group.

The invention further relates to polymerisable liquid crystal material comprising one or more mono-, oligo- or polymers according to the invention.

The invention further relates to an anisotropic polymer film with charge transport properties obtainable from the polymerisable liquid crystal material.

The invention further relates to the use of mono-, oligo- and polymers according to the invention as semiconductors or charge transport materials in optical, electrooptical or electronic devices, like for example components of integrated circuitry, field effect transistors (FET) for example as thin film transistors in flat panel display applications or for Radio Frequency Identification (RFID) tags, and in semiconducting components for organic light emitting diode (OLED) applications, electroluminescent display devices, backlights, photovoltaic or sensor devices.

The invention further relates to a field effect transistor (FET), for example as a component of integrated circuitry, as a thin film transistor in flat panel display applications, or in a Radio Frequency Identification (RFID) tag, a OLED, an electroluminescent device, a RFID tag, backlights, photovoltaic or sensor devices, or electro-photographic recording devices comprising one or more mono-, oligo- or polymers according to the invention.

The invention further relates to a security marking or device comprising one or more mono-, oligo- or polymers, a polymerisable material, a polymer film, a FET or a RFID tag according to the invention, respectively.

The invention further relates to mono-, oligo- and polymers, a material or polymer film according to the invention, which are oxidatively or reductively doped to form conducting ionic species.

The invention further relates to a charge injection layer, planarising layer, antistatic film or conducting substrate or pattern for electronic applications or flat panel displays, comprising mono-, oligo- or polymers, a material or polymer film according to the invention.

The invention further relates to a method of forming an oligomer or polymer, comprising a difluorovinyl-(hetero)arylene group as recurring units, wherein a solution of a metallorganic compound is treated with a nickel or palladium catalyst.

A further aspect of the invention relates to a key intermediate compound of the inventive method.

DETAILED DESCRIPTION OF THE INVENTION

The mono-, oligo- and polymers according to the invention comprise one or more identical or different recurring units of formula I:

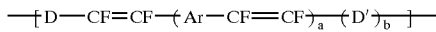

I wherein

D, D' are independently of each other a group of the following formulae 1 to 4:

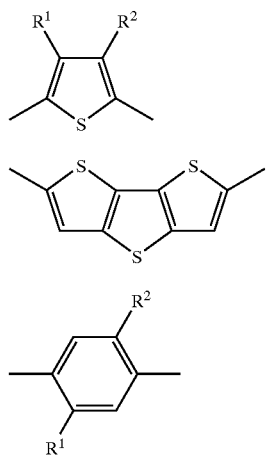

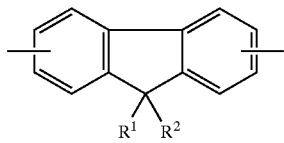

4

$R^1$, $R^2$ are independently of each other halogen, straight chain, branched or cyclic alkyl with 1 to 20 C-atoms, which may be unsubstituted, mono- or poly-substituted by F, Cl, Br, I, —CN and/or —OH, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH═CH— or —C≡C— in such a manner that O and/or S atoms are not linked directly to one another, or optionally substituted aryl or heteroaryl, or one of $R^1$ and $R^2$ also H, $R^0$ and $R^{00}$ are independently of each other H or alkyl with 1 to 12 C-atoms, Ar is a bivalent mono-, bi- or tricyclic aromatic or heteroaromatic group with up to 25 C atoms that may also comprise condensed, i.e. fused, rings and preferably 1–3 fused rings, and is optionally substituted with one or more halogen and/or straight chain, branched or cyclic alkyl groups having 1 to 20 C atoms, which is unsubstituted, mono- or poly-substituted by F, Cl, Br, I, and/or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH═CH— or C≡C— in such a manner that O and/or S atoms are not linked directly to one another, a, b are independently of each other 0 or 1.

The mono-, oligo- and polymers according to the invention are especially useful as semiconductors and charge carrier materials in that they have high charge carrier mobilities.

The oligo- and polymers according to the invention, especially those with D=thiophenylene according to formula 1, can be synthesized with a high to very high degree of regioregularity, showing a high packing density and advantageous microstructure.

Furthermore the oligo- and polymers according to the invention, especially those wherein $R^1$ and/or $R^2$ is an optionally substituted alkyl group, are in general soluble and therefore processable in an easy and economic manner.

Hereafter preferred groups, substituents and indices are described relating to the foregoing and following formulae.

Preferred meanings of D and/or D' are the thiophene and dithienothiophene group according to formulae 1 and 2. The thiophene group according to formula 1 is especially preferred.

$R^1$ and/or $R^2$ are preferably straight chain, branched or cyclic $C_{1-20}$ alkyl, in which one or more H-atoms may be substituted by fluorine, $C_{2-20}$ alkenyl, $C_{2-20}$ alkynyl, $C_{1-20}$ alkoxy, $C_{1-20}$ thioether, $C_{1-20}$ ester, $C_{1-20}$ amino or F. Very preferably $R^1$ is H or F and/or $R^2$ is straight chain alkyl with 1 to 12 C-atoms, in which one or more H-atoms may substituted by fluorine.

Preferably D' has the same meaning as D, including the mirror image of the meaning of D. Furthermore preferred meanings of Ar are those given for D, D'.

The difluorovinylidene linker group —CF═CF— possesses preferably the E- or trans-configuration.

Particularly preferred are mono-, oligo- and polymers according to the invention comprising at least one reactive group that is capable of a polymerisation or crosslinking reaction.

Further preferred are mono-, oligo- and polymers according to the invention that are mesogenic or liquid crystalline.

Further preferred are oligo- and polymers comprising at least two recurring units, at least one of which is a recurring unit according to the invention.

Especially preferred are mono-, oligo- and polymers of formula II:

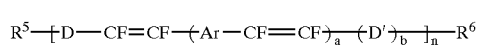

II wherein D, D', Ar, a and b are as defined in formula I, n is an integer from 1 to 5000, $R^5$ and $R^6$ are independently of each other H, halogen, $Sn(R^0)_3$ or straight chain, branched or cyclic alkyl with 1 to 20 C-atoms, which may be unsubstituted, mono- or poly- substituted by F, Cl, Br, I, —CN and/or —OH, it being also possible for one or more non-adjacent $CH_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or denote P—Sp—X, P is a polymerisable or reactive group, Sp is a spacer group or a single bond, and X is —O—, —S—, —OCH$_2$—, —CH$_2$O—, —CO—, —COO—, —OCO—, —OCO—O—, —CO—NR$^0$—, —NR$^0$—CO—, —OCH$_2$—, —CH$_2$O—, —SCH$_2$—, —CH$_2$S—, —CH=CH—COO—, —OOC— CH=CH— or a single bond, wherein $R^0$ and $R^{00}$ are as defined above and wherein the recurring units —[—D—CF=CF—(Ar—CF=CF)$_a$ —(D')$_b$]— can be identical or different.

In the oligo- and polymers of the present invention the recurring units —[—D—CF=CF—(Ar—CF=CF)$_{a}$—(D')$_b$]— in case of multiple occurrence can be selected of formula I independently of each other, so that an oligo- or polymer may comprise identical or different recurring units —[—D— CF=CF—(Ar—CF=CF)$_a$—(D')$_b$]—. The oligo- and polymers thus include homopolymers and copolymers like for example statistically random copolymers, for example with a monomer sequence such as —D—CF=CF—Ar—CF=CF—(D')$_b$—(D')$_b$—CF=CF—Ar— CF=CF—D—, alternating copolymers, for example with a monomer sequence such as —D—CF=CF—Ar—CF=CF—(D')$_b$—D—CF=CF—Ar— CF=CF—(D')$_b$—, and block copolymers, for example with a monomer sequence such as —D—CF=CF—D—CF=CF—Ar—CF=CF—Ar—CF=CF— (D')$_b$—(D')$_b$—, wherein the groups —D—CF=CF—, —Ar—CF=CF— and —D'— form a conjugated system together.

Especially preferred is the homopolymer.

Further preferred are mono-, oligo- and polymers comprising one or more recurring units —[—D—CF=CF— (Ar—CF=CF)$_a$—(D')$_b$]—, wherein a=1 and b=0, very preferably consisting exclusively of such recurring units.

Further preferred are mono-, oligo- and polymers comprising one or more recurring units —[—D—CF=CF— (Ar—CF=CF)$_a$—(D')$_b$]—, wherein a=0 and b=0, very preferably consisting exclusively of such recurring units.

Further preferred are mono-, oligo- and polymers comprising one or more recurring units —[—D—CF=CF— (Ar—CF=CF)$_a$—(D')$_b$]—, wherein a=b=1, very preferably consisting exclusively of such recurring units.

Further preferred are mono-, oligo- and polymers wherein n is an integer greater than 1, n is an integer from 2 to 5000, in particular from 30 to 1000, n is an integer from 2 to 5, n is an integer from 1 to 15 and one or both of $R^5$ and $R^6$ denote P—Sp—X, n is an integer from 2 to 5000 and $R^5$ and $R^6$ have one of the meanings of $R^1$, the molecular weight is from 30000 to 300000, Aryl and heteroaryl preferably denote a mono-, bi- or tricyclic aromatic or heteroarmatic with up to 25 C atoms, wherein the rings may be fused, in which the heteroaromatic groups contain at least one hetero ring atom, preferably selected from N, O and S. The aryl and heteroaryl groups are optionally substituted with one or more of F, Cl, Br, I, CN and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, $R^1$, $R^2$ are selected from $C_1$-$C_{20}$-alkyl that is optionally substituted with one or more fluorine atoms, $C_1$-$C_{20}$-alkenyl, $C_1$-$C_{20}$-alkynyl, $C_1$-$C_{20}$-alkoxy, $C_1$-$C_{20}$-thioether, $C_1$-$C_{20}$-silyl, $C_1$-$C_{20}$-ester, $C_1$-$C_{20}$-amino $C_1$-$C_{20}$-fluoroalkyl, and optionally substituted aryl or heteroaryl, $R^5$ and $R^6$ are selected from H, halogen, $C_1$-$C_{20}$-alkyl that is optionally substituted with one or more fluorine atoms, $C_1$-$C_{20}$-alkenyl, $C_1$-$C_{20}$-alkynyl, $C_1$-$C_{20}$-alkoxy, $C_1$-$C_{20}$-thioether, $C_1$-$C_{20}$-silyl, $C_1$-$C_{20}$-ester, $C_1$-$C_{20}$-amino, $C_1$-$C_{20}$-fluoroalkyl, and optionally substituted aryl or heteroaryl, in particular from H, halogen, $C_1$-$C_{20}$-alkyl and $C_1$-$C_{20}$-alkoxy, Ar has one of the meanings given for D and D', D' has the same meaning as D, if n=1 and a=b=0, at least one of $R^5$ and $R^6$ is different from H, both $R^1$ and $R^2$ are different from H, —CF=CF— are not linked directly together.

A further preferred embodiment of the present invention relates to mono-, oligo- and polymers that are mesogenic or liquid crystalline, in particular those comprising one or more polymerisable groups. Very preferred materials of this type are monomers and oligomers of formula II wherein n is an integer from 1 to 15 and $R^5$ and/or $R^6$ denote P—Sp—X.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high thermal, mechanical and chemical stability.

It is also possible to copolymerise the polymerisable mono-, oligo- and polymers according to the invention with other polymerisable mesogenic or liquid crystal monomers that are known from prior art, in order to induce or enhance liquid crystal phase behaviour.

Thus, another object of the invention is a polymerisable liquid crystal material comprising one or more mono-, oligo- or polymers according to the invention comprising at least one polymerisable group, and optionally comprising one or more further polymerisable compounds, wherein at least one of the polymerisable mono-, oligo- and polymers according to the invention and/or the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred.

Another aspect of the present invention relates to an anisotropic polymer film with charge transport properties obtainable from a polymerisable liquid crystal material as defined above that is aligned in its liquid crystal phase into macroscopically uniform orientation and polymerised or crosslinked to fix the oriented state.

Another aspect of the invention relates to a liquid crystal side chain polymer (SCLCP) obtained from a polymerisable liquid crystal material as defined above by polymerisation or polymeranaloguous reaction. Particularly preferred are SCLCPs obtained from one or more monomers according to formula II wherein one or both of $R^5$ and $R^6$ are a polymerisable or reactive group, or from a polymerisable mixture comprising one or more of such monomers of formula II.

Another aspect of the invention relates to an SCLCP obtained from one or more monomers of formula II wherein one or both of $R^5$ and $R^6$ are a polymerisable group, or from a polymerisable liquid crystal mixture as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

Especially preferred are mono-, oligo- and polymers of the following formulae II1 to II6:

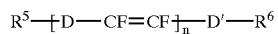

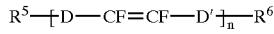

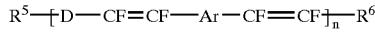

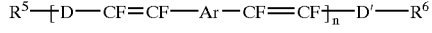

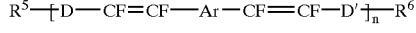

wherein and in the following

D, D' and Ar are as defined in formula I and $R^5$, $R^6$ and n are as defined in formula II.

In the following very preferred mono-, oligo- and polymers according to the invention, especially according to the formulae II1 to II6, are listed. With D=thiophenylene according to formula 1, these very preferred compounds are:

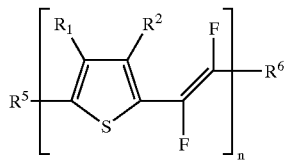

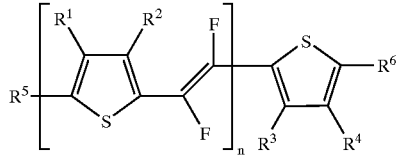

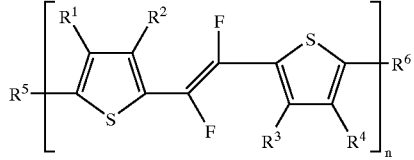

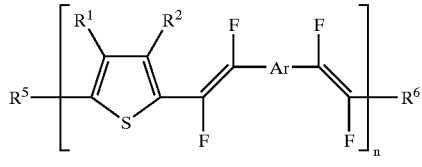

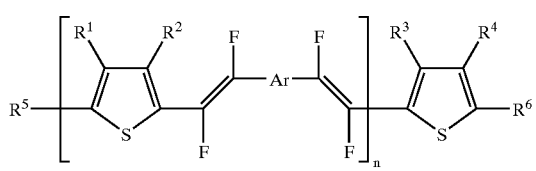

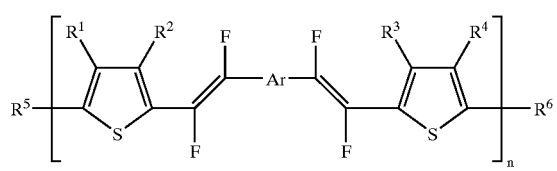

With D=dithienothiophenylene according to formula 2, these very preferred compounds are:
IIIa
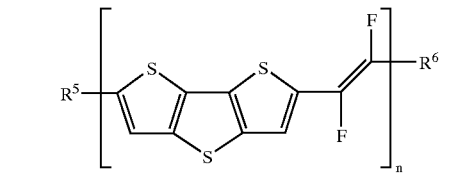
IIIb
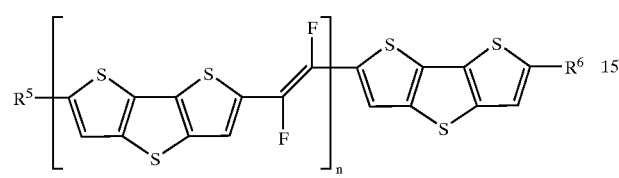
IIIc
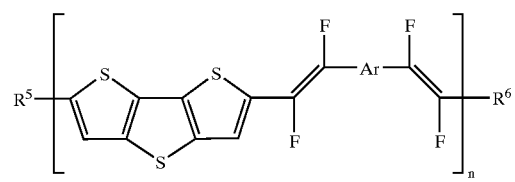
IIId
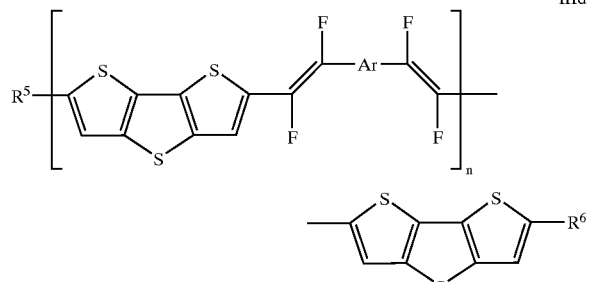
IIIe
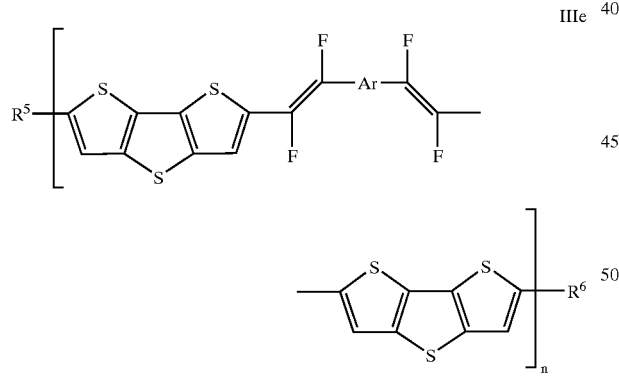
With D=phenylene according to formula 3, these very preferred compounds are:
IVa
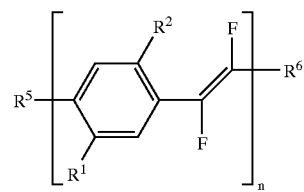
IVb
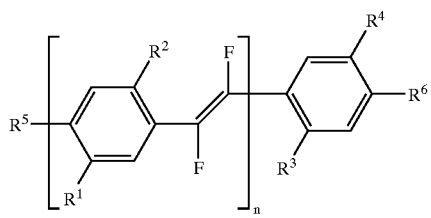
IVc
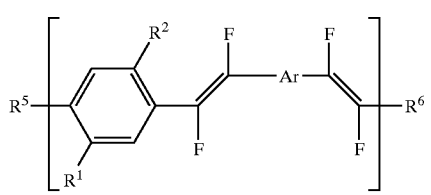
IVd
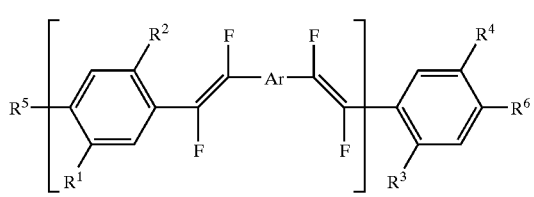
IVe
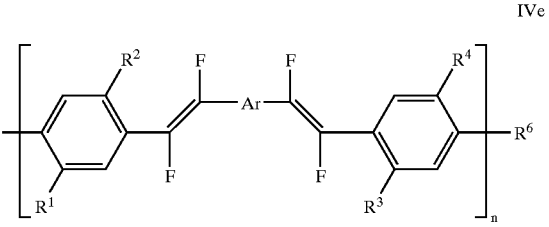
With D=fluorenylene according to formula 4, these very preferred compounds are:
Va
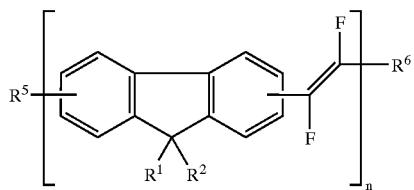
Vb
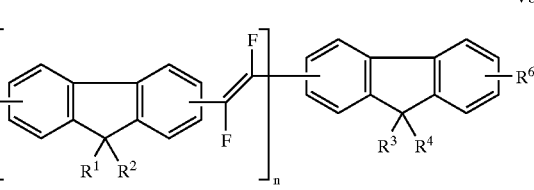
Vc
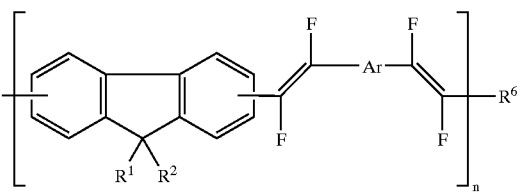

-continued

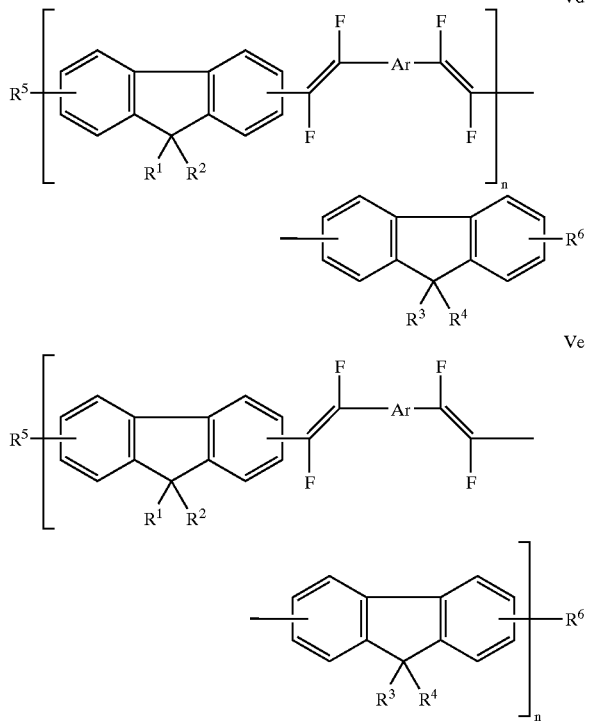

Above and in the following

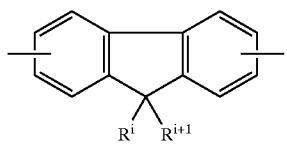

has one of the meanings

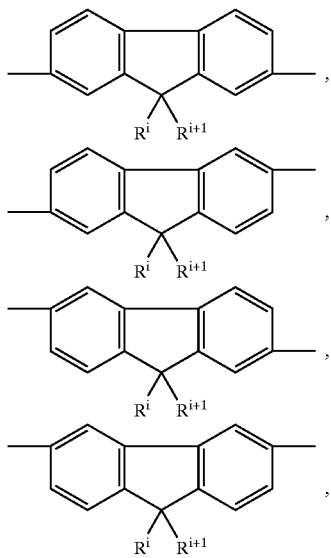

preferably

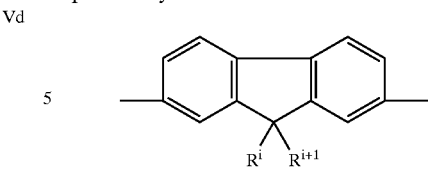

wherein i is 1 or 3.

In these preferred formulae, $R^5$ and $R^6$ are preferably H, F or alkyl with 1–16 C atoms that is optionally fluorinated. Furthermore D' has very preferably the same meaning as D. $R^3$, $R^4$ have preferably the same meanings as $R^1$, $R^2$. Very preferably $R^3$ has the same meaning as $R^2$ and $R^4$ has the same meaning as $R^1$, especially in the compounds of formulae IIe, IIf, IVd, IVe, Vd and Ve.

Especially preferred aryl and heteroaryl groups are phenyl in which, in addition, one or more CH groups may be replaced by N, naphthalene, thiophene, thienothiophene, dithienothiophene, fluorene and oxazole, all of which can be unsubstituted, mono- or polysubstituted with L, wherein L is halogen or an alkyl, alkoxy, alkylcarbonyl or alkoxycarbonyl group with 1 to 12 C atoms, wherein one or more H atoms may be replaced by F or Cl. Very preferably Ar has one of the meanings given for D and D'.

If in the formulae shown above and below one of $R^1$ to $R^6$ is an alkyl or alkoxy radical, i.e. where the terminal $CH_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxadecyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

Fluoroalkyl is preferably $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

Halogen is preferably F or Cl.

The polymerisable or reactive group P is preferably selected from:

$CH_2$=$CW^1$—COO—,

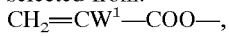
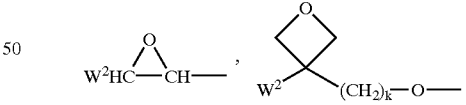

$CH_2$=$CW^2$—$(O)_{k1}$—, $CH_3$—CH=CH—O—, HO—$CW^2W^3$—, HS—$CW^2W^3$—, H$W^2$N—, HO—$CW^2W^3$—NH—, $CH_2$=$CW^1$—CO—NH—, $CH_2$=CH—$(COO)_{k1}$-Phe-$(O)_{k2}$—, Phe-CH=CH—, HOOC—, OCN— and $W^4W^5W^6$Si—, with $W^1$ being H, Cl, CN, phenyl or alkyl with 1 to 5 C-atoms, in particular H, Cl or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and $k_1$ and $k_2$ being independently of each other 0 or 1.

Especially preferred groups P are $CH_2$=CH—COO—, $CH_2$=$C(CH_3)$—COO—, $CH_2$=CH—, $CH_2$=CH—O— and

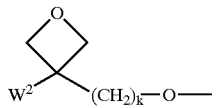

Very preferred are acrylate and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As for the spacer group Sp all groups can be used that are known for this purpose to those skilled in the art. The spacer group Sp is preferably a linear or branched alkylene group having 1 to 20 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)—, —C(halogen)$_2$, —CH(CN)—, —CH=CH— or —C≡C—, or a siloxane group.

Typical spacer groups are for example —($CH_2$)$_p$—, —($CH_2CH_2O$)$_r$—$CH_2CH_2$—, —$CH_2CH_2$—S—$CH_2CH_2$— or —$CH_2CH_2$—NH—$CH_2CH_2$— or —($SiR^0R^{00}$—O)$_p$—, with p being an integer from 2 to 12, r being an integer from 1 to 3 and $R^0$ and $R^{00}$ having the meanings given in formula I.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Further preferred are compounds with one or two groups P—Sp—X wherein Sp and/or X is a single bond.

In case of compounds with two groups P—Sp—X, each of the two polymerisable groups P, the two spacer groups Sp, and the two linkage groups X can be identical or different.

SCLCPs obtained from the inventive compounds or mixtures by polymerisation or copolymerisation have a backbone that is formed by the polymerisable group P in formula II.

The mono-, oligo- and polymers of the present invention can be synthesized according to or in analogy to known methods.

The preferred method according to the invention of forming an oligomer or polymer, comprising at least one recurring units of formula III:

   III wherein D is as defined in formula I and m is an integer ≧2, preferably m≧3, very preferably 5≦m≦5000, comprising a treatment of a solution, that comprises a organometal compound of formula IV:

M—D—CF=CF—Hal   IV wherein D is as defined in formula III and

M is Li, ZnHal' or MgHal' and

Hal, Hal' are independently of each other Cl or Br, preferably Cl, with at least one nickel and/or palladium catalyst.

The treatment of the organometal compound of formula IV with the at least one catalyst, preferably zero valent nickel and/or palladium catalyst, results in the oligomer or polymer of formula III via reaction at the Hal-substituent at the vinylene group. A high to very high regioregularity, especially with a head-to-tail orientation, is yielded. The respective oligo- and polymers show an improved packaging density, an optimised microstructure and a high carrier mobility.

Very preferred catalysts are Pd(PtBu$_3$)$_2$, Pd(PPh$_3$)$_2$Cl$_2$, Pd(dppb)Cl$_2$, and Ni(dppb)Cl$_2$, where dppb is 1,4-bis (diphenylphosphino)butane, Ph is phenyl and tBu is tert.-butyl. But also other catalysts, known for the coupling of (hetero)aryl- and/or alkenyl-groups, may be chosen.

The catalyst or the catalysts are employed in a range of 0.1 to 10. mol-%, especially 0.2 to 5 mol-%, compared to the organometal compound.

Preferably the reaction is performed at a temperature between 0° C. and 120° C., very preferably between 20° C. and 100° C. The reacting time is usually between 15 minutes and 36 hours.

Preferred solvents of the organometal compound are alkanes, ethers, and/or aromatic solvents, which may be halogenated, and their mixtures. Especially preferred solvents are tetrahydrofuran and diethylether as well as mixtures thereof.

The performance of the reaction is not critical to the employed pressure. Usually the reaction is taken place at normal pressure.

The concentration of the organometal compound may be varied in a wide region. A preferred range of concentrations is 0.05 to 0.5 mol/l.

The recovering of the product out of the reacting solution is facilitated by precipitation into methanol, followed by soxhlet extraction In a preferred embodiment of this method the organometal compound of formula IV:

M—D—CF=CF—Hal   IV wherein M, D and Hal are as defined above, is formed by lithiation of a compound of formula V:

H—D—CF=CF—Hal   V wherein D and Hal are as defined above.

The key intermediate compound of formula V is also a subject of the invention.

If M is ZnHal' or MgHal', wherein Hal' is as defined above, the resulting intermediate is treated with ZnHal'$_2$ or MgHal'$_2$, respectively, to obtain the compound of formula IV by metathesis. Preferably ZnHal'$_2$ is ZnCl$_2$ and MgHal'$_2$ is MgBr$_2$. The resulting organometal compounds, especially the organozinc compound, is less reactive than the organolithium ones, so that undesired side reactions are reduced.

The lithiation itself is done with reagents and methods, including solvents and reacting conditions, known to the one skilled in the art. Suitable lithiation reagents are e.g. lithium diisopropylamide (LDA) and lithium tetramethylpiperidine (LiTMP). The lithiation is carried out at low temperatures, especially between −120° C. and +20° C.

Further preferred is an embodiment wherein the compound of formula V is synthesized by a method comprising a) forming the respective Grignard or organolithium reagent of a compound of formula VI:

H—D—Hal''   VI wherein D is as defined in formula V and Hal" is Cl or Br, preferably Br, and b) reacting the resulting Grignard or organolithium reagent with a trifluorohaloethylene of the formula VII:

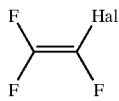

VII wherein Hal is as defined in formula V, preferably Cl.

The formation of the Grignard or organolithium reagent in step a) is done with reagents and methods, including solvents and reacting conditions, known to the one skilled in the art.

The subsequent reacting of the Grignard reagent with the trifluorohaloethylene of the formula VII in step b) is done in the same reacting solution advantageously.

The molar ratio of the Grignard reagent to the trifluorohaloethylene is preferably in the range of about 0,8:1 to 1,3:1, especially about 1:1.

A preferred temperature range for the reaction in step b) is −120° C. to +20° C., especially −80° C. to 0° C.

According to a very preferred embodiment of the above described method, embodiments as well as of the key intermediate of formula V D is a substituted thiophenylene of formula 1:

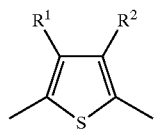

1 wherein $R^1$ and $R^2$ are as defined according to formula I and are non-reactive with the Grignard or organolithium reagent according to embodiment described above, the lithiation reagent according to the first preferred embodiment, the organometal compound of formula IV according to the main method according to the invention.

The inventive method, including preferred embodiments, wherein D is thiophenylene of formula 1, is illustratively shown in scheme 1 and described below.

Scheme 1:

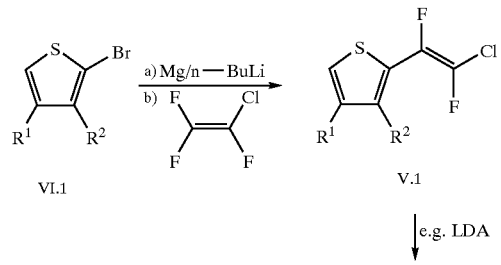

-continued

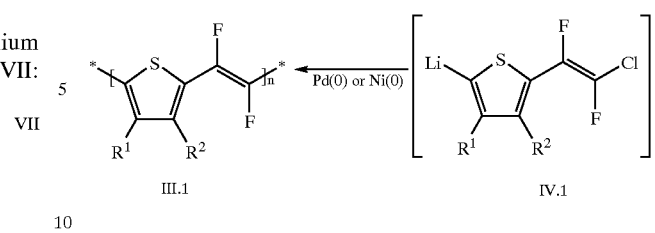

The synthesis of 2-bromo-3-alkylthiophene VI.1 has been reported [see reference 15] and e.g. it is readily available from the bromination of 3-alkylthiophene. Formation of the Grignard or organolithium reagent of VI.1 and reaction with chlorotrifluoroethylene at low temperature affords the key intermediate V.1. Lithiation of V.1 at low temperature e.g. with LDA or LiTMP occurs exclusively at the 5-position. Treatment of this intermediate with zero valent nickel or palladium catalysts affords a regioregular polymer upon warming, via reaction at the vinylchloride. Preferred catalysts include $Pd(dppb)Cl_2$, $Ni(dppb)Cl_2$, $Pd(PPh_3)_2Cl_2$, and $Pd(PtBu_3)_2$. Further variations include metathesis of the organolithium intermediate V.1 with $ZnCl_2$ or $MgBr_2$ to form the respective organozinc or organomagnesium reagent. Again polymer formation occurs after addition of nickel or palladium catalysts to the organometall compound IV.1.

According to scheme 2, the oligomer and polymer III.1 can also be obtained by the Stille coupling of the substituted 2,5-dibromo-thiophene (9) with the bis-organotin reagent (10) [see reference 11].

Scheme 2:

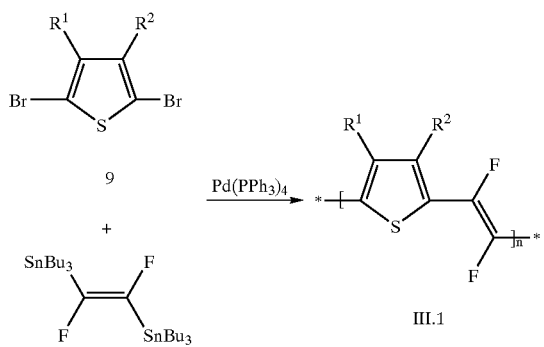

Preferred synthetic routes leading to co-oligomers and co-polymers according to the invention are shown in the following reaction schemes and are described below.

Scheme 3:

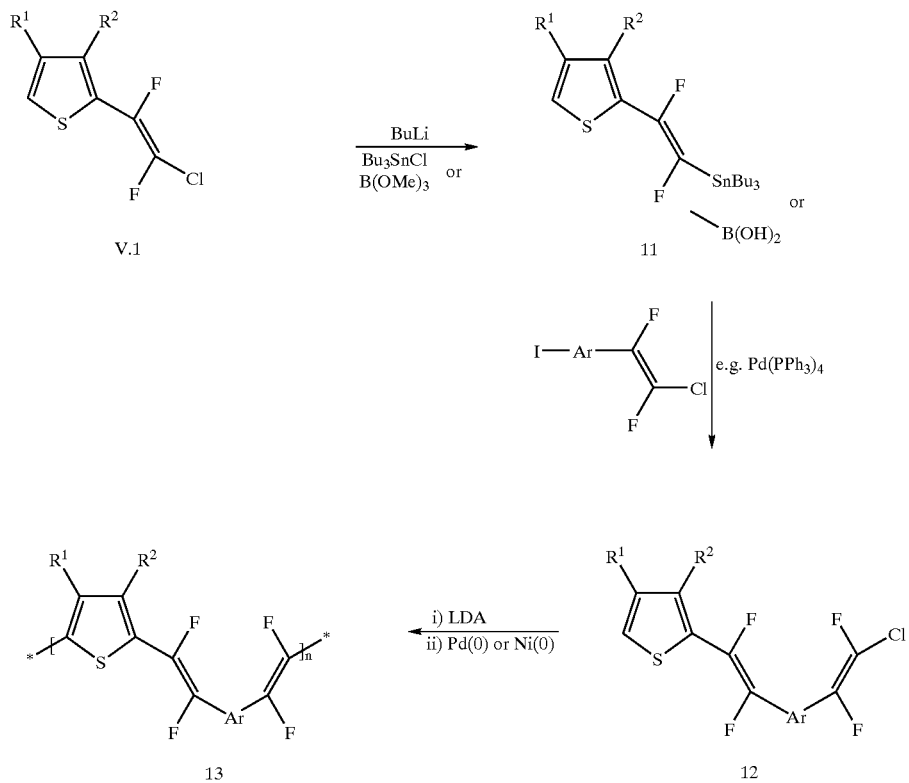

Key intermediate V.1 is lithiated at the vinylic chlorine by treatment with n- or sec-butyllithium (BuLi) at low temperature to form the organolithium. The corresponding Grignard reagent can also be prepared by treatment with magnesium metal. Treatment of the resulting organometallic compound with tributyltin chloride or trimethylborate affords the organotin or boronic acid intermediate (11). Both are stable compounds which can be isolated via the usual techniques. Stille coupling of the organotin compound with an aryl iodide, or Suzuki coupling of the boronic acid with an aryl iodide affords key intermediate 12. This is polymerised by the same procedure as described above to yield an oligomer or polymer 13.

Scheme 4:

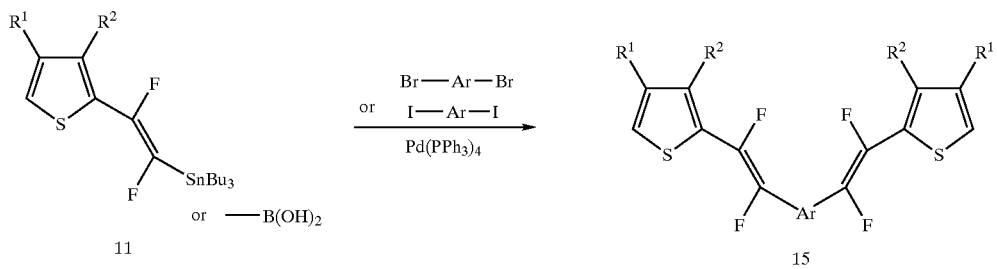

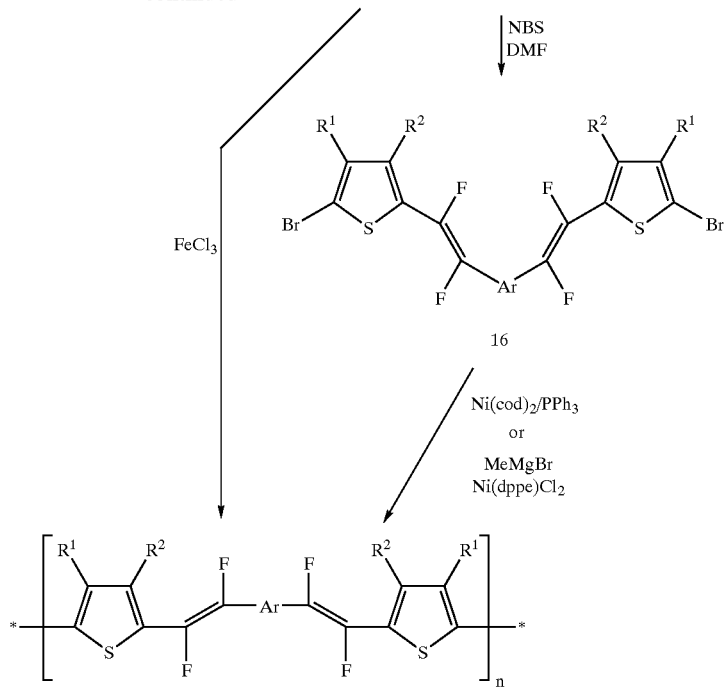

Stille or Suzuki coupling of two equivalents 11 with a diiodoaryl or dibromoaryl unit affords the bis(thienyl)aryl compound 15. This can be directly polymerised by treatment with ferric chloride. Alternatively bromination of the thiophene nucleus in the presence of a double bond can be achieved with N-bromsuccinimide (NBS) in dimethylformamide (DMF) [see reference 11]. Polymerisation of the resulting intermediate 16 then occurs by treatment with bis(1,5-cyclooctadiene) nickel, Ni(COD)$_2$, (Yamomoto coupling) or with one equivalent of methylmagnesiumbromide in the presence of a nickel catalyst, e.g. 1,2-bis(diphenylphosphino)ethane-nickel(II)dichloride Ni(dppe)Cl$_2$ [see reference 16], thus yielding the oligomer or polymer 17.

The reaction schemes, including the descriptions, shown above, may not only be applied to the case, in which D is a thiophenylene group, but also to the other meanings D according to the subformulae 2, 3 and 4, especially to the case in which D is 2,5-disubstituted 1,4-phenylene according to subformula 3.

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g. $Cl^-$, $Br^-$, $I^-$, $I_3^-$, $HSO_4^-$, $SO_4^{2-}$, $NO_3^{31}$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g. $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Br), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns ot tracts in electronic applications such as printed circuit boards and condensers.

Mono-, oligo- and polymers according to the present invention that comprise one or more groups P—Sp—X can be polymerised, or copolymerised with other polymerisable compounds, via the polymerisable group P. This is preferably done by in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45–66.

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75–77, and by T. Uchida and H. Seki in "Liquid Crystals—Applications and Uses Vol. 3", edited by B. Bahadur, World Scientific Publishing, Singapore 1992, pages 1–63. A review of alignment materials and techniques is given by J. Cognard, Mol. Cryst. Liq. Cryst. 78, Supplement 1 (1981), pages 1–77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Mono-, oligo- and polymers comprising one or more groups P—Sp—X can also be copolymerised with polymerisable mesogenic compounds to induce, or, in case of mesogenic materials of formula I, enhance liquid crystal phase behaviour. Polymerisable mesogenic compounds that are suitable as comonomers are known in prior art and disclosed for example in WO 93/22397; EP 0,261,712; DE 195,04,224; WO 95/22586 and WO 97/00600.

SCLCPs can be prepared from the polymerisable compounds or mixtures according to the invention by the methods described above, or by conventional polymerisation techniques which are known to those skilled in the art, including for example radicalic, anionic or cationic chain polymerisation, polyaddition or polycondensation. Polymerisation can be carried out for example as polymerisation in solution, without the need of coating and prior alignment, or polymerisation in situ. It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added, e.g., to polysiloxane backbones with Si—H groups. It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397; EP 0,261,712; DE 195,04,224; WO 95/22586 and WO 97/00600. Typical non mesogenic comonomers are for example alkyl mono- or diacrylates or alkyl mono- or dimethacrylates with alkyl groups of 1 to 20 C atoms, like methyl acrylate or methyl methacrylate, trimethylpropane trimethacrylate or pentaerythritol tetraacrylate.

Especially the oligomers and polymers according to the invention show advantageous solubility properties which allow production processes using solutions of these compounds. Thus films, including layers and coatings, may be generated by low cost production techniques e.g. spin coating. Suitable solvents or solvent mixtures comprise alkanes and/or aromatics, especially their fluorinated derivatives. Preferred solvents are propylene glycol monoethyl acetate, methoxy propanol, ethyl lactate, cyclohexanone and cyclopropanone and mixtures comprising one or more of these solvents.

The mono-, oligo- and polymers according to the invention are useful as optical, electronic and semiconductor materials, in particular as charge transport materials in field effect transistors (FETs), as photovoltaics or sensor materials, for electrophotographic applications, and for other semiconductor applications. Such FETs, where an organic semiconductive material is arranged as a film between a gate-dielectric and a drain and a source electrode, are generally known, e.g. U.S. Pat. No. 5,892,244, WO 00/79617, U.S. Pat. No. 5,998,804, also see references 1, 3 and 10. The solubility properties of these materials according to the invention, allow amenability to solution processing, and therefore low cost, high volume manufacture by techniques such as reel to reel coating is possible. Preferred applications of these FETs are therefore such as integrated circuitry, TFT-displays and security applications. In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques etc.

Alternatively, the mono-, oligo- and polymers according to the invention may be used in organic light emitting devices or diodes (OLEDs), e. g. in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see e. g. Meerholz, Synthetic Materials, 111–112, 2000, 31–34, Alcala, J. Appl. Phys., 88, 2000, 7124–7128 and the literature cited therein.

According to another use, the inventive compounds, materials or films, especially those which show photoluminescent properties, may be employed as materials of light sources, e.g. of display devices such as described in EP 0 889 350 A1 or by C. Weder et al., Science, 279, 1998, 835–837.

Thus another aspect of the invention is a semiconducting component, e.g. a FET, as described above, or in OLED applications like electroluminescent displays or backlights of e.g. liquid crystal displays, in photovoltaic or sensor devices, as electrode materials in batteries, as photoconductors and for electrophotographic applications, comprising one or more mono-, oligo- or polymers, optionally in their doped form, according to the invention.

References

1. H. E. Katz, Z. Bao and S. L. Gilat, *Acc. Chem. Res.*, 2001, 34, 5, 359.
2. S. F. Nelson, Y. Y. Lin, D. J. Gundlach and T. N. Jackson, *Appl. Phys. Lett.*, 1998, 72, 1854.
3. H. Sirringhaus, N. Tessler, R. H. Friend, *Science*, 1998, 280, 1741–1744.
4. H. Sirringhaus, et al., *Nature*, 1999. 401, 685–688.
5. H. Sirringhaus, et al., *Synthetic Metals*, 2000, 111–112, 129–132.
6. H. Sirringhaus, N. Tessler, D. S. Thomas, P. J. Brown, R. H. Friend, *Adv. Solid State Phys.*, 1999, 39, 101.
7. Z. Bao, A. Dodabalapur and A. J. Lovinger, *Appl. Phys. Lett.*, 1996, 69, 4108.
8. L. Robitaille and M. Leclerc, *Macromol.* 1994, 27, 1847–1851.
9. S. Doi et al., *Synthetic Metals*, 1993, 55–57, 4174–4179.
10. H. Fuchigami et al., *Appl. Phys. Lett.*, 1993, 63, 1372–1374.
11. R. D. McCullough and R. S. Loewe, *Chem. Mater.*, 2000, 12, 3214–3221.
12. U.S. Pat. No. 5,892,244.
13. WO 96/21659.
14. A. B. Shtrarev and Z. Chvatal, *J. Org. Chem.*, 1997, 62, 5608–5614.
15. Hoffmann et al., *Synthetic Communications*, 1999, 29, 1607–1610.
16. Loewe, R. S., S. M. Khersonsky, and R. D. McCullough, *Advanced Materials* 1999, 11(3), 250–253.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The foregoing disclosure of all cited applicaitons, patents and publications, and of corresponding European Application No. 01117650.0, filed Jul. 25, 2001, is hereby incorporated by reference.

EXAMPLES

Example 1

2-(2'-chloro-1,2-difluorovinyl)-3-hexylthiophene (V.1, $R^1$=H, $R^2$=hexyl)

In a dry 3-necked flask under nitrogen n-BuLi (1.6M in hexanes, 15 ml) was diluted wit dry tetrahydrofuran (THF) (30 ml) and cooled to −78 C. "-Bromo-3-hexylthiophene (5.0 g, 0.02 mol) was added dropwise over 15 minutes (min). The reaction was stirred at −78 C. for 2 hours (h). In a separate flask chlorotrifluoroethylene (15 ml, excess) was liquified and stirred at −42 C. The solution of thiophene was added via a cannula over 30 min, and the reaction stirred at −42 C. for 4 h. The reaction was warmed to room temperature (RT) and stirred for a further 14 h. The reaction was quenched with sat, ammonium chloride and extracted with THF (3×50 ml). The combined organics were washed with brine, dried ($Na_2SO_4$), filtered and concentrated under reduced pressure to afford a yellow oil (4.70 g). This was further purified by filtration through silica (eluent: petrol) to afford 2-(2'-chloro-1,2-difluorovinyl)-3-hexylthiophene (4.50 g, 85%) as a mixture of cis/trans isomers (1:4). Purity high-performance liquid chromatography (HPLC)=96%. Microspherical silica alumina (MS (EI)) 264 (d, $M^+$). High vacuum distillation through a packed column with a reflux ratio head (0.1 mbar, 70–71 C.) afforded 2.6 g of product. Purity (HPLC) >99%. $^{19}F$ nuclear magnetic resonance (NMR) revealed the expected signals, $^1H$ and $^{13}C$ NMR were complicated by the presence of cis/trans isomers.

Example 2

5-(2'-chloro-1,2-difluorovinyl)-3-hexylthiophene (V.1, $R^1$=hexyl, $R^2$=H)

A solution of 3-hexylthiophene (30 g, 0179 mol) in anhydrous petrol (40–60 C., 100 ml) was cooled to −10 C. and diisopropylamine (freshly distilled, 18.1 g, 0179 mol) and tetramethylethylenediamine (TMEDA) (33 g, 028 mol) were added. N-BuLi (1.6M in hexanes, 113 ml, 0.18 mol) was added dropwise over 30 min at −10 C. The solution was warmed to 0 C. over 1 h, and then added via cannula to a solution of chlorotrifluorethylene at −78 C. The reaction was warmed to RT over 2 h and stirred for a further 16 h. The reaction was quenched with sat, ammonium chloride and extracted with THF (3×50 ml). The combined organics were washed with brine, dried ($Na_2SO_4$), filtered and concentrated under reduced pressure to afford a yellow oil (47 g). High vacuum distillation through a packed column with a reflux ratio head (0.1 mbar, 70–71 C.) afforded 13.0 g of product. Purity (HPLC) >99%. MS (EI) 264 (d, $M^+$). $^{19}F$ NMR revealed the expected signals, $^1H$ and $^{13}C$ NMR were complicated by the presence of cis/trans isomers.

Example 3

Poly(difluorovinyl)-3-hexylthiophene

To a solution of freshly distilled diisopropylamine (0.23 g, 3.11 mmol) in dry THF under nitrogen at 0 C. was added n-BuLi (1.56M in hexane, 1.9 ml, 9.98 mmol). The solution was stirred for 10 min at 0 C. and then cooled to −78 C. 2-(2'-Chloro-1,2-difluorovinyl)-3-hexylthiophene (0.75 g, 2.83 mmol) was added dropwise and the reaction stirred at −78 C. for 4 h. A solution of ZnCl₂ in diethyl ether (1M, 3.1 ml, 3.1 mmol) was added and the reaction stirred for a further 1 h. In a separate schlenk flask a solution of 1,4-bis (diphenylphosphino)butane (55.6 mg, 0.13 mmol) and tris (benzylideneacetone)dipalladium (59.7 mg, 0.065 mmol) in anhydrous NMP (5 ml) was prepared. The organozinc reagent was transferred into the schlenk flask by cannula and the mixture heated to 100 C. for 18 h. The reaction was cooled and poured into methanol and the resulting precipitate filtered. This was washed with methanol to afford poly(difluorovinyl)-3-hexylthiophene (0.11 g, 16%). Gel permeation chromatography indicates molecular number (Mn)=1900, molecular weight (Mw)=9600.

The preceding examples can be repeated with similar success by substituting the generically or specifically described reactants and/or opertiang conditions of this invention for those used in the preceding examples.

From the foregoing descriptions, one skilled in the art can easily ascertain the essential characteristics of this invention and, without departing from the spirit and scope thereof, can make various changes and modifications of the invention to adapt it to varous usages and conditions.

What is claimed is:

1. A monomeric, oligomeric or polymeric compound comprising one or more identical or different recurring units of formula I:

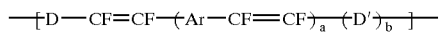

wherein

D, D' are independently of each other a group of the following formulae 1 to 3:

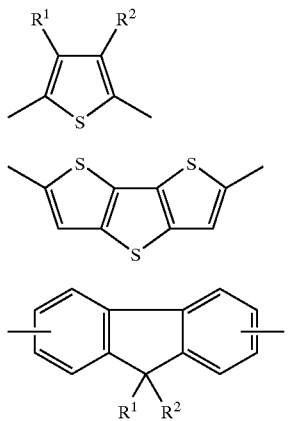

R¹, R² are independently of each other halogen, straight chain, branched or cyclic alkyl with 1 to 20 C-atoms, which are unsubstituted, mono- or poly-substituted by F, Cl, Br, I, —CN and/or —OH, and in which one or more non-adjacent CH₂ groups are, optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or one of R¹ and R² also H, R⁰ and R⁰⁰ are independently of each other H or alkyl with 1 to 12 C-atoms, Ar is a bivalent mono-, bi- or tricyclic aromatic or heteroaromatic group with up to 25 C atoms that may also comprise condensed rings and is optionally mono- or poly-substituted with F, Cl and/or groups R¹ as defined above, and a, b are independently of each other 0 or 1.

2. A compound according to claim 1, wherein said compound contains at least one reactive group that is capable of a polymerization or crosslinking reaction.

3. A compound according to claim 1, wherein said compound is mesogenic or liquid crystalline.

4. A compound according to claim 1, wherein said compound comprises at least two recurring units, at least one of which is a recurring unit of formula I.

5. A compound according to claim 1, wherein said compound is of formula II:

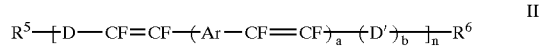

wherein D, D', Ar, a and b are as defined in formula I, n is an integer from 1 to 5000, R⁵ and R⁶ are independently of each other H, halogen, Sn(R⁰)₃ or straight chain, branched or cyclic alkyl with 1 to 20 C-atoms, which is unsubstituted, mono- or poly-substituted by F, Cl, Br, I, —CN and/or —OH, and in which one or more non-adjacent CH₂ groups are, optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or denote P—Sp—X, P is a polymerizable or reactive group, Sp is a spacer group or a single bond, and X is —O—, —S—, —OCH₂—, —CH₂O—, —CO—, —COO—, —OCO—, —OCO—O—, —CO—NR⁰—, —NR⁰—CO—, —OCH₂—, —CH₂O—, —SCH₂—, —CH₂S—, —CH=CH—COO—, —OOC—CH=CH— or a single bond, wherein R⁰ and R⁰⁰ are as defined in formula I and wherein the recurring units —[—D—CF=CF—(Ar—CF=CF)ₐ—(D')ᵦ]— can be identical or different.

6. A compound according to claim 5, selected from the following formulae II1 to II6:

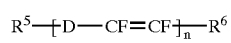

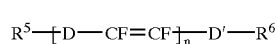

wherein

D, D' and Ar are as defined in formula I and

R⁵, R⁶ and n are as defined in formula II.

7. A compound according to claim 5, wherein at least one of R⁵ and R⁶ is P—Sp—X.

8. A compound according to claim 5, wherein P is CH₂=CW¹—COO—,

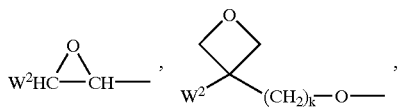

CH₂=CW²—(O)$_{k_1}$—, CH₃—CH=CH—O—, HO—CW²W³—, HS—CW²W³—, HW²N—, HO—CW²W³—NH—, CH₂=CW¹—CO—NH—, CH₂=CH—(COO)$_{k_1}$-Phe-(O)$_{k_2}$—, Phe-CH=CH—, HOOC—, OCN— or W⁴W⁵W⁶Si—,
- W¹ is H, Cl, CN, phenyl or alkyl with 1 to 5 C-atoms,
- W² and W³ are, independently of each other, H or alkyl with 1 to 5 C-atoms,
- W⁴, W⁵ and W⁶ are, independently of each other, Cl, oxaalkyl or oxacarbonylalkyl with 1 to 5 C-atoms, Phe is 1,4-phenylene, and
- k₁ and k₂ are independently of each other 0 or 1.

9. A compound according to claim 8, wherein W₂ and W₃ are, independently, of each other methyl, ethyl or n-propyl.

10. A compound according to claim 5, wherein n is an integer from 1 to 15.

11. A compound according to claim 5, wherein R⁵ and R⁶ are independently of each other halogen, straight chain, branched or cyclic alkyl with 1 to 20 C-atoms, which are unsubstituted, mono- or poly-substituted by F, Cl, Br, I, —CN and/or —OH, and in which one or more non-adjacent CH₂ groups are, optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or one of R⁵ and R⁶ is also H.

12. A compound according to claim 1, wherein D' has the same meaning as D.

13. A compound according to claim 1, wherein Ar has one of the meanings of D, D' given in formula I.

14. A polymerizable liquid crystal material comprising at least one compound according to claim 1 having at least one polymerizable group, and at least one further polymerizable compound, wherein at least one of said compound or said further polymerizable compound is mesogenic or liquid crystalline.

15. An anisotropic polymer film with charge transport properties obtainable from a polymerizable liquid crystal material according to claim 14 that is aligned in its liquid crystal phase into macroscopically uniform orientation and polymerized or crosslinked to fix the oriented state.

16. A field effect transistor (FET), an OLED, an electroluminescent device, a semiconductor, a charge transport material, a RFID tag, a backlight, a photovoltaic or a sensor device, a security marking or device, or an electrophotographic recording device comprising a polymer film of claim 15.

17. A film according to claim 15 which is oxidatively or reductively doped to form conducting ionic species.

18. A field effect transistor (FET), an OLED, an electroluminescent device, a semiconductor, a charge transport material, a RFID tag, a backlight, a photovoltaic or a sensor device, a security marking or device, or an electrophotographic recording device comprising a polymerizable material of claim 14.

19. A side chain liquid crystal polymer obtained by polymerization of at least one compound according to claim 1 with at least one additional mesogenic or non-mesogenic comonomer.

20. A polymer according to claim 19 which is oxidatively or reductively doped to form conducting ionic species.

21. A field effect transistor (FET), an OLED, an electroluminescent device, a semiconductor, a charge transport material, a RFID tag, a backlight, a photovoltaic or a sensor device, a security marking or device, or an electrophotographic recording device comprising a polymer according to claim 19.

22. A side chain liquid crystal polymer obtained by grafting at least one compound according to claim 1, to a polymer backbone in a polymer analogous reaction.

23. A field effect transistor (FET), an OLED, an electroluminescent device, a semiconductor, a charge transport material, a RFID tag, a backlight, a photovoltaic or a sensor device, a security marking or device, or an electrophotographic recording device comprising a polymer according to claim 22.

24. A polymer according to claim 22 which is oxidatively or reductively doped to form conducting ionic species.

25. A field effect transistor (FET), an OLED, an electroluminescent device, a semiconductor, a charge transport material, a RFID tag, a backlight, a photovoltaic or a sensor device, a security marking or device, or an electrophotographic recording device comprising at least one compound of claim 1.

26. A compound polymer according to claim 1, which is oxidatively or reductively doped to form a conducting ionic species.

27. A charge injection layer, a planarizing layer, an antistatic film or a conducting substrate or pattern for an electronic application or a flat panel display, comprising a compound according to claim 26.

28. A method of forming an oligomer or polymer, comprising recurring units of formula III:

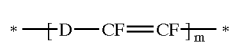

wherein D is

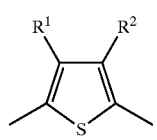

and m is an integer ≥2, comprising a treatment of a solution comprising an organometal compound with a nickel or palladium catalyst.

29. A method according to claim 28 wherein the organometal compound is of a formula IV:

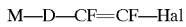

wherein D is as defined in formula III and
M is Li, ZnHal' or MgHal' and
Hal, Hal' are independently of each other Cl or Br,
is formed by lithiation of the compound of formula V:

wherein D and Hal are defined as in formula IV and,
if M is ZnHal' or MgHal', wherein Hal' is as defined in formula IV the resulting intermediate is treated with ZnHal'₂ or MgHal'₂, respectively, to obtain the compound of formula IV by metathesis.

30. A method according to claim 29 wherein the compound of formula V is synthesized by:

a) forming the respective Grignard or organolithium reagent of a compound of formula VI:

$$H-D-Hal'' \qquad VI$$

wherein D is as defined in formula V and Hal'' is Cl or Br and b) reacting the resulting Grignard or organolithium reagent with a trifluorohaloethylene of the formula VII:

$$\underset{F}{\overset{F}{\diagup}}C=C\underset{F}{\overset{Hal}{\diagdown}} \qquad VII$$

wherein Hal is as defined in formula V.

31. A method according to claim 29 wherein D is a substituted thiophenylene of formula 1:

[Structure 1: thiophene with $R^1$, $R^2$ substituents]

wherein $R^1$ and $R^2$ are are independently of each other halogen, straight chain, branched or cyclic alkyl with 1 to 20 C-atoms, which are unsubstituted, mono- or poly-substituted by F, Cl, Br, I, —CN and/or —OH, and in which one or more non-adjacent $CH_2$ groups are, optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or one of $R^1$ and $R^2$ is also H, and are non-reactive with the Grignard reagent as defined in formula VI and the organometal compound of formula IV.

32. A compound of formula V:

$$H-D-CF=CF-Hal \qquad V$$

wherein D is as defined in formula 1 and Hal is Cl or Br.

33. A monomeric, oligomeric or polymeric compound comprising one or more identical or different recurring units of formula I:

$$-\!\!\left[D-CF=CF-\!\!\left(Ar-CF=CF\right)_a\!\!\left(D'\right)_b\right]\!\!- \qquad I$$

wherein

D,D' are independently of each other a group of the following formulae 1 to 3

[Structure 1: thiophene with $R^1$, $R^2$ substituents]

[Structure 2: fused bithiophene]

[Structure 3: fluorene with $R^1$, $R^2$ substituents at 9-position]

$R^1$, $R^2$ are independently of each other halogen, straight chain, branched or cyclic alky with 1 to 20 C-atoms, which are unsubstituted, mono- or poly-substituted by F, Cl, Br, I, —CN and/or —OH, and in which one or more non-adjacent $CH_2$ groups are, optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, wherein both $R^1$ and $R^2$ are different from H, $R^0$ and $R^{00}$ are independently of each other H or alkyl with 1 to 12 C- atoms, Ar is a bivalent mono-, bi- or tricyclic aromatic or heteroaromatic group with up to 25 C atoms that may also comprise condensed rings and is optionally mono- or poly-substituted with F, Cl, and/or R1 as define above, and a, b are independently of each other 0 or 1.

34. A compound according to claim 33, wherein said compound is of formula II:

$$R^5-\!\!\left[D-CF=CF-\!\!\left(Ar-CF=CF\right)_a\!\!\left(D'\right)_b\right]_n\!\!-R^6 \qquad II$$

wherein D, D', Ar, a and b are as defined in formula I, n is an integer greater than 1, $R^5$, $R^6$ are independently of each other H, halogen, $Sn(R^0)_3$ or straight chain, branched or cyclic alkyl with 1 to 20 C-atoms, which is unsubstituted, mono- or poly-substituted by F, Cl, Br, I, —CN and/or —OH, and in which one or more non-adjacent $CH_2$ groups are, optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or denote P—Sp—X, P is a polymerizable or reactive group, Sp is a spacer group or a single bond, and X is —O—, —S—, —$OCH_2$—, —$CH_2O$—, —CO—, —COO—, —OCO—, —OCO—O—, —CO—$NR^0$—, —$NR^0$—CO—, —$OCH_2$—, —$CH_2O$—, —$SCH_2$—, —$CH_2S$—, —CH=CH—COO—, —OOC—CH=CH— or a single bond, wherein $R^0$ and $R^{00}$ are as defined in formula I and wherein the recurring units $$-\!\!\left[D-CF=CF-\!\!\left(Ar-CF=CF\right)_a\!\!\left(D'\right)_b\right]\!\!-$$

can be identical or different.

* * * * *

UNITED STATES PATENT AND TRADEMARK OFFICE
CERTIFICATE OF CORRECTION

PATENT NO.    : 6,824,706 B2
DATED         : November 30, 2004
INVENTOR(S)   : Martin Heeney Page 1 of 1

It is certified that error appears in the above-identified patent and that said Letters Patent is hereby corrected as shown below:

Column 32,
Line 26, reads "R1" should read -- $R^1$ --

Signed and Sealed this

Twenty-second Day of March, 2005

JON W. DUDAS
*Director of the United States Patent and Trademark Office*